United States Patent
Iizuka et al.

(10) Patent No.: US 10,165,999 B2
(45) Date of Patent: Jan. 1, 2019

(54) RADIOLOGICAL-IMAGE ACQUISITION DEVICE

(71) Applicant: SHARP KABUSHIKI KAISHA, Sakai, Osaka (JP)

(72) Inventors: Kunihiko Iizuka, Sakai (JP); Shigenari Taguchi, Sakai (JP); Katsuhisa Kashiwagi, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

(21) Appl. No.: 15/739,890

(22) PCT Filed: Mar. 10, 2016

(86) PCT No.: PCT/JP2016/057492
§ 371 (c)(1),
(2) Date: May 4, 2018

(87) PCT Pub. No.: WO2017/002403
PCT Pub. Date: Jan. 5, 2017

(65) Prior Publication Data
US 2018/0249976 A1    Sep. 6, 2018

(30) Foreign Application Priority Data
Jun. 30, 2015 (JP) ................. 2015-132061

(51) Int. Cl.
*G01T 1/24* (2006.01)
*A61B 6/00* (2006.01)
(Continued)

(52) U.S. Cl.
CPC ............... *A61B 6/52* (2013.01); *A61B 6/54* (2013.01); *G01T 1/24* (2013.01); *G01T 7/00* (2013.01); *H04N 5/32* (2013.01); *H04N 5/341* (2013.01)

(58) Field of Classification Search
CPC .... A61B 6/52; A61B 6/54; G01T 1/24; H04N 5/32; H04N 5/341
See application file for complete search history.

(56) References Cited

U.S. PATENT DOCUMENTS

| | | |
|---|---|---|
| 2002/0024601 A1 | 2/2002 | Kaifu et al. |
| 2004/0135911 A1 | 7/2004 | Nathan et al. |
| | (Continued) | |

FOREIGN PATENT DOCUMENTS

| | | |
|---|---|---|
| JP | 2002-051265 A | 2/2002 |
| WO | 2012/004928 A1 | 1/2012 |

OTHER PUBLICATIONS

Taghibakhsh, F.; Karim, K.S., "Two-Transistor Active Pixel Sensor for High Resolution Large Area Digital X-ray Imaging," IEEE International Electron Devices Meeting 2007, pp. 1011, 1014, Dec. 10-12, 2007.

*Primary Examiner* — Casey Bryant
(74) *Attorney, Agent, or Firm* — ScienBiziP, P.C.

(57) ABSTRACT

Improvement of a frame rate and suppression of power consumption are intended. A radiological-image acquisition device (100) includes a plurality of pixels, a capacitive element (1a) that accumulates electric charge corresponding to a dose (X) of radiation, and a read control unit (read element control unit 22, reset element control unit 23) that reads, from at least one pixel (active pixel 10) that is not subjected to initialization in two or more frames, an output (output voltage Vout) corresponding to the electric charge.

4 Claims, 9 Drawing Sheets

(51) Int. Cl.
*H04N 5/341* (2011.01)
*G01T 7/00* (2006.01)
*H04N 5/32* (2006.01)

(56) References Cited

U.S. PATENT DOCUMENTS

| | | | |
|---|---|---|---|
| 2005/0259170 A1 | 11/2005 | Kaifu et al. | |
| 2010/0237252 A1* | 9/2010 | Jin | H01J 37/244 |
| | | | 250/370.08 |
| 2011/0199523 A1* | 8/2011 | Tanabe | H04N 5/32 |
| | | | 348/300 |
| 2012/0127337 A1 | 5/2012 | Okada et al. | |

\* cited by examiner

RADIOLOGICAL-IMAGE ACQUISITION DEVICE

TECHNICAL FIELD

The present invention relates to an image acquisition device using radiation, in particular, X-rays.

BACKGROUND ART

A radiological-image acquisition panel in which sensor elements that output electric charges (electric signals) corresponding to a dose of radiation, in particular, X-ray radiation that has been radiated to a subject are arranged two-dimensionally has been developed. The sensor elements are provided respectively in a plurality of pixels disposed in a two-dimensional matrix on a substrate (panel). In such a radiological-image acquisition panel, the electric charge is accumulated in a capacitive element provided in each of the pixels and a thin film transistor (TFT) element performs control to read an output corresponding the accumulated electric charge from each of the pixels.

In particular, there has been an increasing demand to reduce effects of noise that is generated, for example, in a circuit for reading an output corresponding to the accumulated electric charge. Upon such a demand, a radiological-image acquisition panel of an active pixel type in which a TFT element as an amplification element is further provided in each of the pixels and the output is amplified and transmitted to the circuit, and an image acquisition device including the panel have been actively developed.

For example, PTL 1 and NPL 1 disclose an active pixel sensor that includes a TFT for AMP (amplification of output), a TFT for READ (read of output), and a TFT for RESET (reset of the active pixel sensor). Here, the reset of the active pixel sensor refers to returning a gate voltage of the TFT for AMP to an initial electric potential that has been set, so that the drain-source current of the TFT for AMP has a predetermined value. As an active pixel sensor of the related art, there is one in which the three TFTs and the sensor element are connected as illustrated in FIG. 1. As a radiological-image acquisition panel of an active pixel type according to the related art, there is one in which active pixel sensors of FIG. 1 are disposed in a two-dimensional matrix on a substrate and which includes a Reset signal generation circuit, a Read signal generation circuit, a control circuit, and a current/voltage conversion amplifier as illustrated in FIG. 2. Note that, for convenience of description, 4×4=16 active pixel sensors in total are illustrated in FIG. 2. The Reset signal generation circuit generates and outputs signals Reset_1' to Reset_4' for resetting the active pixel sensors. The Read signal generation circuit generates and outputs signals Read_1' to Read_4' for reading output currents Iout_1' to Iout_4' from the active pixel sensors.

Next, FIG. 3 illustrates an example of a timing chart of an image acquisition operation by an image acquisition device including an image acquisition panel illustrated in FIG. 2. As illustrated in FIG. 3, the image acquisition device resets capacitive elements of all the active pixel sensors for each time required to read data for one two-dimensional image. Further, FIG. 4 illustrates another example of a timing chart of an image acquisition operation by the image acquisition device. As illustrated in FIG. 4, the image acquisition device suspends the read of data for a two-dimensional image and resets the active pixel sensors, and then performs the read again. Such an operation is performed on a row-by-row basis of the active pixel sensors and is performed for the active pixel sensors of all the rows in the time required to read data for one two-dimensional image.

CITATION LIST

Patent Literature

PTL 1: US Patent Application Publication No. US 2004/0135911 A1 (published on Jul. 15, 2004)

Non Patent Literature

NPL 1: Taghibakhsh, F.; Karim, K. S., "Two-Transistor Active Pixel Sensor for High Resolution Large Area Digital X-ray Imaging," IEEE International Electron Devices Meeting 2007, pp. 1011, 1014, 10-12, December 2007

SUMMARY OF INVENTION

Technical Problem

However, PTL 1 and NPL 1 disclose that the reset of the active pixel sensors and the read of output are performed within a time (read time) in which the read of output is performed, but there is no disclosure about a technique of controlling a terminal for RESET so as not to perform the reset in the read time. Thus, an image acquisition device including a plurality of active pixel sensors described above has a problem that when all the active pixel sensors are reset for each read time, the read time becomes longer by the time required for the reset and power consumption of the image acquisition device also increases compared to a case where there exists an active pixel sensor that is not reset. An image acquisition device including a radiological-image acquisition panel of an active pixel type according to the related art also has a problem similar to the aforementioned problem because all the active pixel sensors are reset for each time required to read data for one two-dimensional image.

The invention was made to solve the aforementioned problems and an object thereof is to provide a radiological-image acquisition device that realizes improvement of a frame rate and suppression of power consumption by reducing a total time for acquiring data for a two-dimensional image.

Solution to Problem

In order to solve the aforementioned problems, a radiological-image acquisition device according to an aspect of the invention is a radiological-image acquisition device that acquires a two-dimensional image according to a dose of radiation that has been radiated to a subject. The radiological-image acquisition device includes a plurality of pixels disposed two-dimensionally; a capacitive element in each of the plurality of pixels, the capacitive element, when the radiation is incident on the plurality of pixels, accumulating electric charge corresponding to the dose for the pixel in at least two sequential frames; and a read control unit that, with respect to at least one of the plurality of pixels, does not perform initialization of the at least one pixel but reads, from the pixel, a first output and a second output which correspond to the accumulated electric charge in each of a first frame and a second frame that constitute the two frames.

Advantageous Effects of Invention

According to an aspect of the invention, it is possible to realize improvement of a frame rate and suppression of power consumption by not initializing at least one pixel in each of a first frame and a second frame that are sequential frames.

DESCRIPTION OF EMBODIMENTS

[Embodiment 1]

Hereinafter, an embodiment of the invention will be described in detail with reference to FIG. 1 and FIGS. 5 to 8.

<Configuration of Radiological-Image Acquisition Device>

Figure 5:
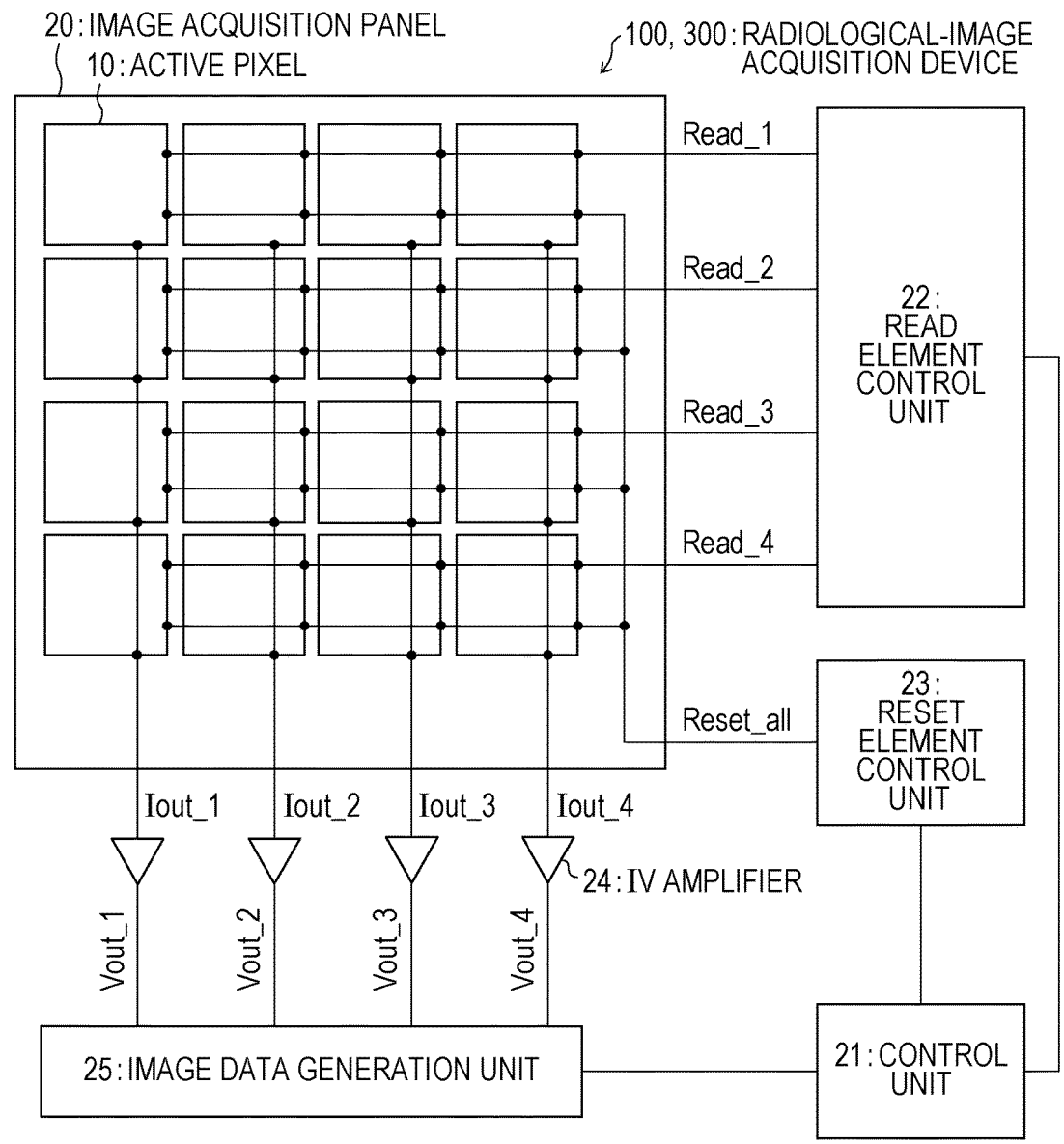
FIG. 5 is a circuit diagram illustrating a main part of the radiological-image acquisition device according to Embodiment 1 of the invention.

First, a main configuration of a radiological-image acquisition device 100 will be described. FIG. 5 is a circuit diagram illustrating a main part of the radiological-image acquisition device 100. The radiological-image acquisition device 100 performs acquisition of a moving image by continuously generating two-dimensional image data corresponding to a dose X of radiation that has been radiated to a subject. As illustrated in FIG. 5, the radiological-image acquisition device 100 includes an image acquisition panel 20, a control unit 21, a read element control unit (read control unit) 22, a reset element control unit (read control unit) 23, a current/voltage conversion amplifier (hereinafter, abbreviated as an "IV amplifier") 24, and an image data generation unit (output generation unit) 25.

Figure 2:
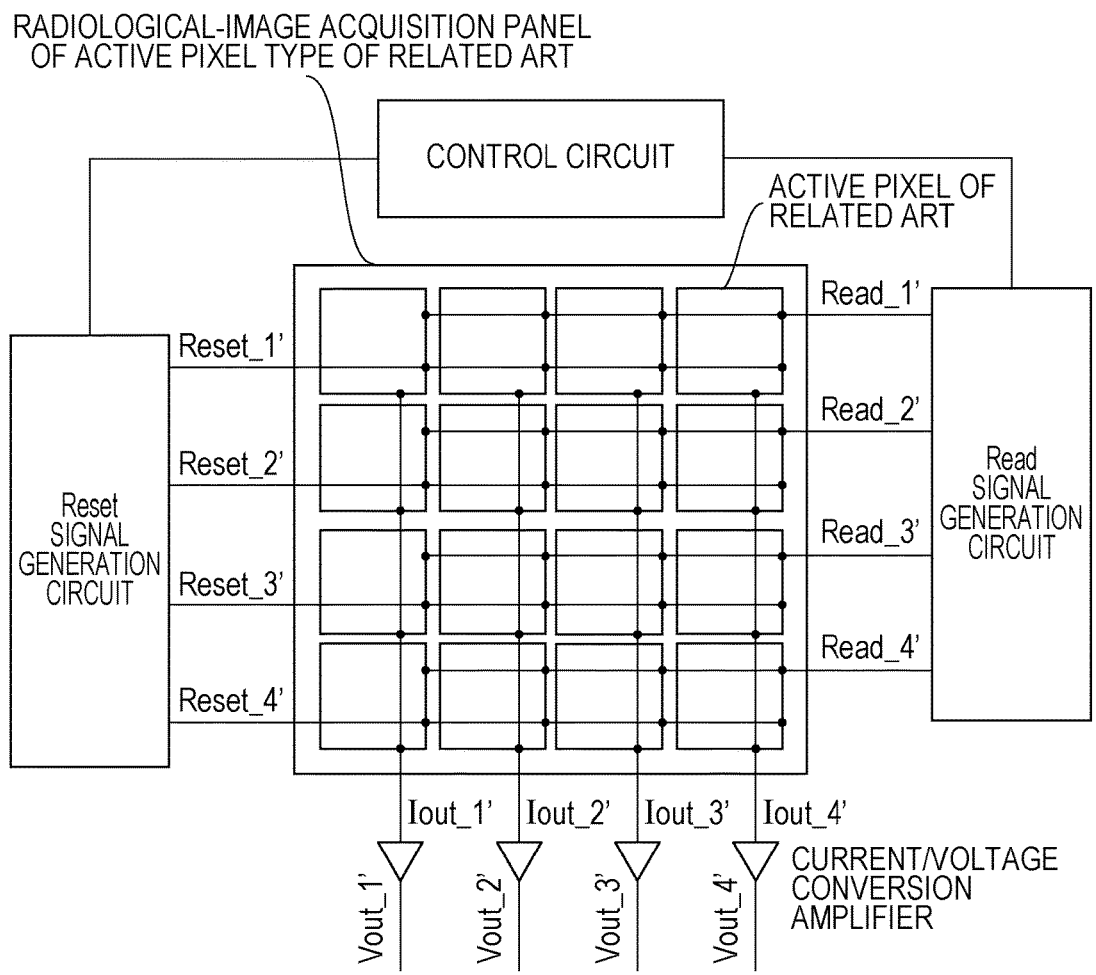
FIG. 2 is a circuit diagram illustrating a main part of an image acquisition device that includes a radiological-image acquisition panel of an active pixel type according to the related art.
Figure 3:
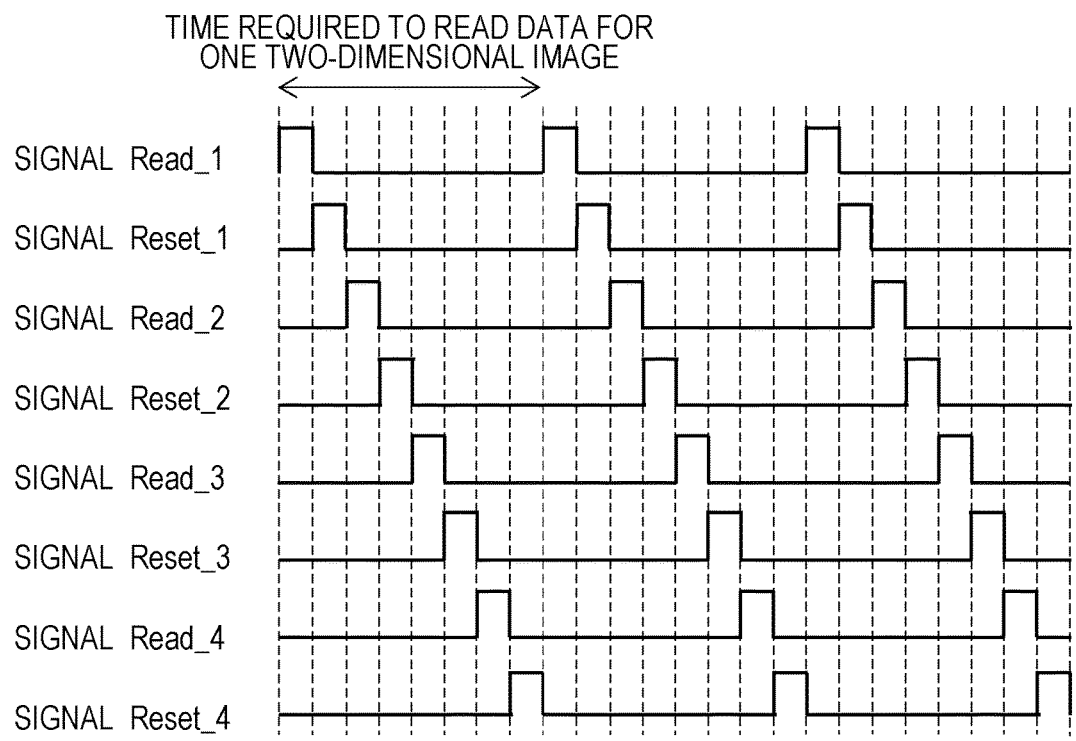
FIG. 3 illustrates an example of a timing chart of an image acquisition operation by the image acquisition device according to the related art.
Figure 4:
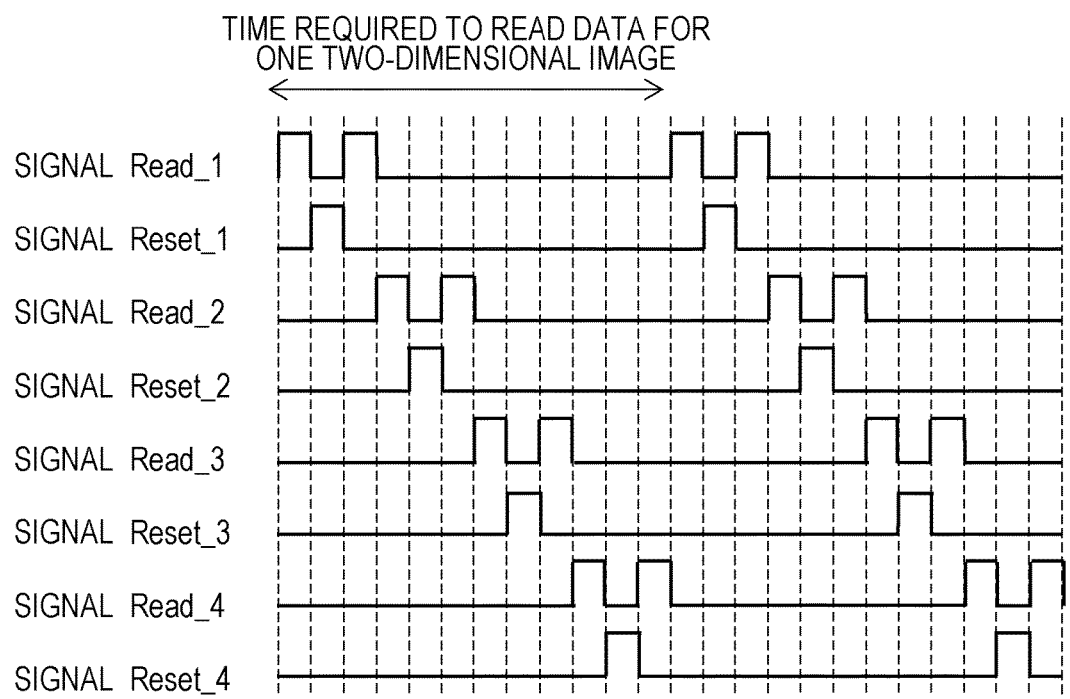
FIG. 4 illustrates another example of a timing chart of an image acquisition operation by the image acquisition device according to the related art.

The image acquisition panel 20 is a flat substrate and $n^2$ active pixels (a plurality of pixels) 10 in total are arranged in a matrix of n rows×n columns in plan view. Note that, the number and arrangement of the active pixels 10 are not particularly limited as long as they are arranged two-dimensionally, and FIG. 2 exemplifies an array of 4 rows×4 columns to simply the illustration.

The control unit 21 performs control of the read element control unit 22, the reset element control unit 23, and the image data generation unit 25 and generally controls the radiological-image acquisition device 100.

The read element control unit 22 outputs read signals Read_1 to Read_4 to gate electrodes of read elements 3 (described later with reference to FIG. 1) of each row (a row includes four active pixels 10) of the active pixels 10 and thereby controls read of output currents Iout_1 to Iout_4 by the read elements 3. Each of the read signals Read_1 to Read_4 has a high-level (High) period during which the read is executed and a low-level (Low) period during which the read is suspended.

The reset element control unit 23 outputs a reset signal Reset_all to gate electrodes of all reset elements 4 (described later with reference to FIG. 1) and thereby controls initialization of the active pixels 10 by the reset elements 4. The reset signal Reset_all has a high-level (High) period during which the initialization is executed and a low-level (Low) period during which the initialization is suspended.

The IV amplifier 24 converts the output currents Iout_1 to Iout_4 output from the read elements 3 into output voltages Vout_1 to Vout_4 and outputs the output voltages Vout_1 to Vout_4 to the image data generation unit 25.

On the basis of the output voltages Vout_1 to Vout_4 to be input, the image data generation unit 25 generates two-dimensional image data having a resolution of 4×4 which is proportional to a variation ΔX of the dose X of radiation incident on each of the active pixels 10. Note that, data processing by the image data generation unit 25 will be described later.

A capacitive element 1a, the read element 3, the reset element 4, the active pixel 10, and the initialization of the active pixel 10 will be described in detail below.

<Configuration of Active Pixel>

Figure 1:
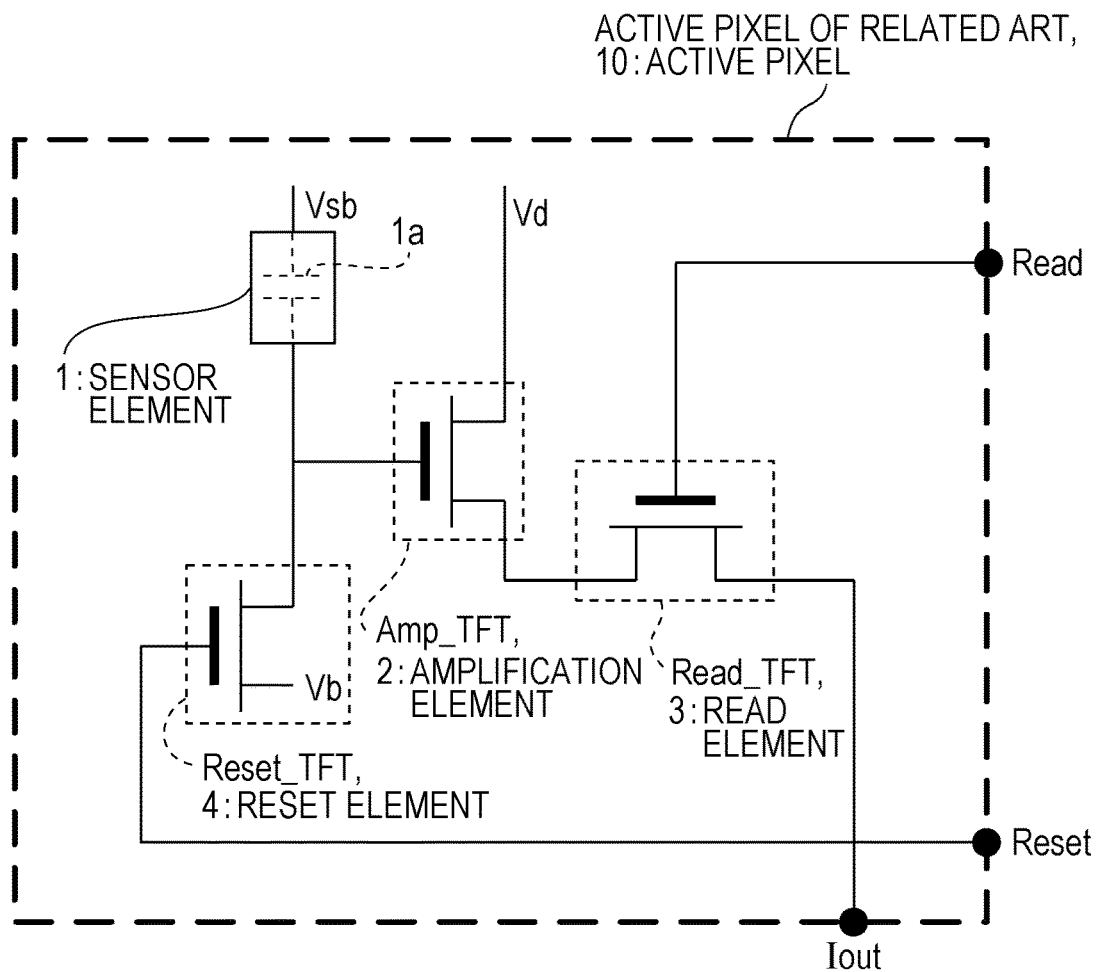
FIG. 1 is a circuit diagram of a main part of an active pixel according to the related art and an active pixel that is included in a radiological-image acquisition device according to Embodiment 1 of the invention.

Next, a main configuration of the active pixel 10 will be described. FIG. 1 is a circuit diagram illustrating a main part of the active pixel 10. The active pixel 10 converts the dose X of radiation that has been radiated to a subject into an output current Iout that is used to generate two-dimensional image data and outputs the output current Iout. As illustrated in FIG. 1, the active pixel 10 includes the sensor element 1, the amplification element 2, the read element 3, and the reset element 4.

Note that, description will be given in the present embodiment and each subsequent embodiment by assuming that a TFT element is used as each of the amplification element 2, the read element 3, and the reset element 4.

The sensor element 1 is an element which detects that the radiation radiated to the subject is incident on the active pixel 10 and includes therein the capacitive element 1a that accumulates electric charge corresponding to the dose X. The sensor element 1 may be, for example, a photodiode and the capacitive element 1a may be constituted by, for example, capacitance between terminals of the sensor element 1. The sensor element 1 has an input terminal to which a bias voltage Vsb is applied from a bias power supply (not illustrated) and has an output terminal which is connected to the gate electrode of the amplification element 2 and a drain electrode of the reset element 4. The sensor element 1 applies, to the gate electrode of the amplification element 2, an electric signal corresponding to the electric charge accumulated in the capacitive element 1a while the reset element 4 is turned off.

In the amplification element 2, a voltage (gate voltage) of the gate electrode changes in accordance with the electric charge accumulated in the capacitive element 1a. The amplification element 2 outputs, to a source electrode of the read element 3, the change in the gate voltage as a change in amplified current between the drain and source. The amplification element 2 has a source electrode to which a power supply voltage Vd is applied from a power supply (not illustrated) of the amplification element 2 and has a drain electrode connected to the source electrode of the read element 3.

In response to a read signal Read output from the read element control unit 22, the read element 3 reads an electric signal amplified by the amplification element 2 as an output current Iout and outputs the output current Iout to the IV amplifier 24.

Specifically, when the read signal Read input to the gate electrode of the read element 3 is High, an emitter and a collector of the read element 3 are electrically connected, and the read element 3 outputs the output current Iout. On the other hand, when the read signal Read is Low, the emitter and the collector are brought into an interruption state. That is, the read element 3 functions as a switch element, and executes the read in an on state and suspends the read in an off state.

The reset element 4 initializes the active pixel 10 in response to the reset signal Reset_all output from the reset element control unit 23. Here, the initialization of the active pixel 10 refers to returning an electric potential of the capacitive element 1a to an initial electric potential Vb with which a voltage between the gate and source of the amplification element 2 slightly exceeds a predetermined threshold. The initial electric potential Vb is set to about Vb=3 V, for example, when the amplification element 2 is an N-type TFT element and the predetermined threshold is 2 V.

A reason why the active pixel 10 is initialized is that when the electric potential of the capacitive element 1a becomes excessively high due to the electric charge being excessively accumulated, the output current Iout output from the amplification element 2 is saturated and an output voltage Vout is thereby saturated. Thus, by returning the electric potential of the capacitive element 1a to the initial electric potential Vb before the electric potential becomes excessively high, the amplification element 2 is able to be operated with an appropriate signal amplification rate.

Specifically, when the reset signal Reset_all input to the gate electrode of the reset element 4 is High, an emitter and a collector of the reset element 4 are electrically connected, and the capacitive element 1a is connected to the initial electric potential Vb. On the other hand, when the reset signal Reset_all is Low, the emitter and the collector are brought into an interruption state. That is, the reset element 4 functions as a switch element, and executes the initialization in an on state and suspends the initialization (that is, electric charge is accumulated by the capacitive element 1a) in an off state.

<Image Acquisition Operation by Radiological-Image Acquisition Device>

Figure 6:
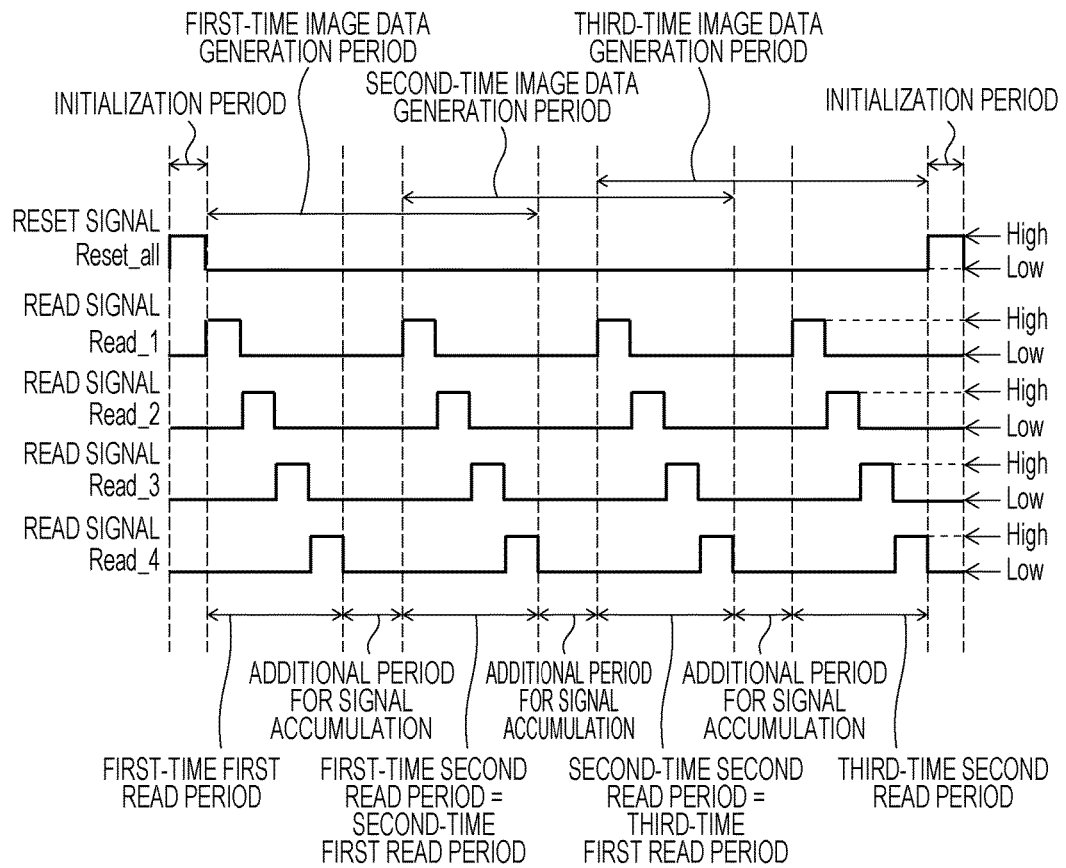
FIG. 6 illustrates a timing chart of an image acquisition operation by the radiological-image acquisition device according to Embodiment 1 of the invention.
Figure 7:
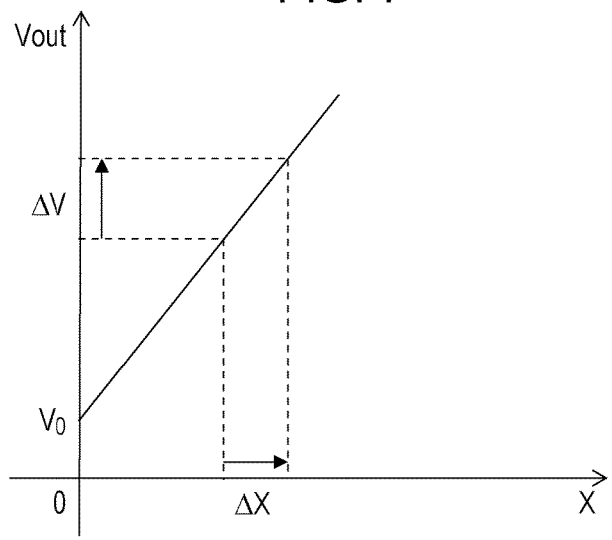
FIG. 7 is a graph indicating a relation between a dose of radiation incident on an active pixel included in the radiological-image acquisition device according to Embodiment 1 of the invention and an output voltage from the active pixel.

Next, an image acquisition operation by the radiological-image acquisition device 100 will be described with reference to FIGS. 6 and 7. FIG. 6 illustrates a timing chart of the image acquisition operation by the radiological-image acquisition device 100. FIG. 7 is a graph indicating a relation between the dose X of radiation incident on the active pixel 10 and the output voltage Vout.

The image acquisition operation by the radiological-image acquisition device 100 is constituted by two phases of an initialization period and an image data generation period as illustrated in FIG. 6. The image data generation period is constituted by three phases of a first read period, a second read period, and an additional period for signal accumulation.

The additional period for signal accumulation is a period that is added, as appropriate, so as to reserve a signal accumulation time for obtaining signal intensity required, and there is a case where a time length thereof is zero, that is, the additional period is not set. The time length of the additional period for signal accumulation is set as a sub-frame. Note that, the additional period for signal accumulation functions also as a redundant period to ensure constancy of a frame cycle.

Each of a time length of a lapsed time of the first read period and a time length of the second red-out period is set as one frame. Here, one frame specifically refers to a time required to read output voltages Vout_1 to Vout_4 from respective columns of the active pixels 10. The time length of the first read period is set as a first frame and the time length of the second read period is set as a second frame.

Note that, in the following description, an output current and an output voltage of the active pixel 10 of an (i)th row and a (j)th column that are read during an (n)th-time High period of a read signal Read_i in a state where the active pixels 10 are not initialized after being initialized first are respectively set as Iout(i, j, n) and Vout(i, j, n). The dose of radiation incident on the active pixel 10 of the (i)th row and the (j)th column up to the (n)th-time read is set as X(i, j, n).

(Initialization Period)

First, before the image data generation period starts, the reset element control unit 23 outputs a first-time High reset signal Reset_all from output terminals connected to the gate electrodes of all the reset elements 4 to turn on all the reset elements 4 and initializes all the active pixels 10. Here, an initialization time (that is, a time length of the initialization period) required to initialize the active pixels 10 is determined on the basis of capacitance of the capacitive elements 1a, resistance of a line that applies the initial electric potential Vb, and impedance of the power supply source of the initial electric potential Vb.

By performing control as described above, two-dimensional image data having the resolution of 4×4 is able to be continuously generated over a plurality of frames smoothly without initializing the active pixels 10 immediately after the image data generation period starts.

In the present embodiment, each time three image data generation periods required to generate data for three two-dimensional images from a total of 16 active pixels 10 that are arranged in a 4×4 matrix have lapsed, all the active pixels 10 are initialized. That is, in the present embodiment, an initialization cycle for initializing all the active pixels 10 is a sum of time lengths of four frames (a time length of a plurality of frames, refer to FIG. 6) and three sub-frames (refer to FIG. 6). The reset element control unit 23 initializes all the active pixels 10 altogether at a time when the four frames have lapsed.

However, the initialization cycle of the active pixels 10 is not limited to the aforementioned case. That is, a purpose of the initialization is to prevent saturation of the output voltage Vout, and the saturation is caused when the capacitive elements 1a is brought into a saturated state (a state in which electric charge is not able to be accumulated). Alternatively, the saturation is caused when the voltage applied to the gate electrode of the amplification element 2 becomes excessively high and the output current Iout of the amplification element 2 is saturated. Thus, the initialization cycle may be determined by calculating in advance a time required until a quantity of the electric charge accumulated in the capacitive element 1a that has been initialized once reaches a threshold (for example, a quantity of the electric charge that is slightly smaller than a quantity of the electric charge with which the capacitive element 1a is brought into the saturated state). For example, the initialization cycle (the number of frames) may be determined by assuming a maximum input of the dose X of radiation incident on each of the active pixels 10 and obtaining in advance how long it takes to reach the threshold when the maximum input is retained.

It is not necessary to initialize all the active pixels 10 altogether for each initialization cycle as in the present embodiment, and the active pixels 10 of a row or a plurality of rows may be sequentially initialized, for example, for each frame (refer to Embodiment 2). In other words, the reset element control unit 23 is only required to initialize all the active pixels 10 within the initialization cycle so that all the active pixels 10 are initialized before the initialization cycle ends.

Note that, in order to achieve the object of the invention, i.e., improvement of a frame rate, the initialization cycle needs to be defined as a time length of a plurality of frames or a sum of time lengths of a plurality of frames and a plurality of sub-frames.

(Image Data Generation Period)

After the initialization of all the active pixels 10 ends, an operation of generating two-dimensional image data having the resolution of 4×4 starts. That is, a first-time image data generation period starts. Specifically, the reset element control unit 23 outputs a first-time Low reset signal Reset_all from the output terminals and turn off all the reset elements 4. At the same time, the read element control unit 22 sequentially outputs first-time High read signals Read_1, Read_2, Read_3, and Read_4 from the output terminals connected to the gate electrodes of the read elements 3 in respective rows of the active pixels 10.

Then, an output current Iout(i, 1, 1), an output current Iout(i, 2, 1), an output current Iout(i, 3, 1), and an output current Iout(i, 4, 1) are sequentially read via the respective read elements 3 in each column (a column includes four active pixels 10) of the active pixels 10.

The four output currents Iout that are read are respectively converted by the IV amplifier 24 into an output voltage Vout(i, 1, 1), an output voltage Vout(i, 2, 1), an output voltage Vout(i, 3, 1), and an output voltage Vout(i, 4, 1) and output to the image data generation unit 25. When all the four output voltages Vout (first output) are input to the image data generation unit 25, a first-time first read period ends.

After the first-time first read period ends, a first-time second read period starts. Also in the second read period, the reset element control unit 23 and the read element control unit 22 perform signal output control in a similar manner to that of the first read period. Four output voltages Vout (second output) of an output voltage Vout(i, 1, 2), an output voltage Vout(i, 2, 2), an output voltage Vout(i, 3, 2), and an output voltage Vout(i, 4, 2) are sequentially output to the image data generation unit 25.

Next, the image data generation unit 25 generates data for one two-dimensional image on the basis of the output voltages Vout that are read in the first-time first read period and the output voltages Vout that are read in the first-time second read period.

Specifically, the image data generation unit 25 calculates a variation $\Delta X$ by assuming that a variation $\Delta X$ of the dose X of the radiation incident on the active pixel 10 and a variation $\Delta V$ of the output voltage Vout corresponding to the dose X have a proportional relation ($\Delta V = \alpha \cdot \Delta X$, constant of proportionality; $\alpha$) as illustrated in FIG. 7. The image data generation unit 25 generates two-dimensional image data proportional to the calculated variation $\Delta X$ for each of the active pixels 10 and acquires data for one two-dimensional image having the resolution of 4×4.

That is, when an output voltage of the active pixel 10 of the (i)th row and the (j)th column read in a first-time High period of the read signal Read_i is set as Vout(i, j, 1) and an output voltage read in a second-time High period of the read signal Read_i is set as Vout(i, j, 2), a relation of Vout(i, j, 2)−Vout(i, j, 1)=$\alpha$\{X(i, j, 2)−X(i, j, 1)\} is satisfied. Thus, by performing calculation of Vout(i, j, 2)−Vout(i, j, 1), the variation $\Delta X$ of the dose X of the radiation incident on the active pixel 10 from the first read period to the second read period is calculated.

Note that, a time to read the output voltage Vout of each of the active pixels 10, that is, the High period of the read signal Read is sufficiently shorter than a time of incidence of the radiation on the active pixel 10. Thus, in the present embodiment and each subsequent embodiment, the dose X of the incident radiation and the output voltage Vout corresponding to the dose X are assumed to be constant in a period (a High period of the read signal Read_i) to read the output voltage Vout from the active pixel 10 of the (i)th row and the (j)th column during the first read period and the second read period.

When the image data generation unit 25 acquires data for one two-dimensional image having the resolution of 4×4 as described above, the first-time second read period ends and the first-time image data generation period ends.

Also in second-time and subsequent image data generation periods, the image data generation unit 25 acquires data for two-dimensional images having the resolution of 4×4 one by one in a similar manner to the aforementioned manner.

That is, when an output voltage of the active pixel 10 of the (i)th row and the (j)th column read in an (n)th-time High period of the read signal Read_i is set as Vout(i, j, n) and an output voltage read in an (n+1)th-time High period of the read signal Read_i is set as Vout(i, j, n+1), a relation of Vout(i, j, n+1)−Vout(i, j, n)=$\alpha$\{X(i, j, n+1)−X(i, j, n)\} is satisfied. Thus, by performing calculation of Vout(i, j, n+1)−Vout(i, j, n), the variation $\Delta X$ is calculated.

In other words, by obtaining a difference between the output voltage (second amplification output) Vout(i, j, n+1) and the output voltage (first amplification output) Vout(i, j, n) that are read by the read element control unit 22, the image data generation unit 25 generates the variation $\Delta X$ (read output corresponding to the dose of the radiation). The image data generation unit 25 then generates the two-dimensional image data proportional to the variation $\Delta X$ for each of the active pixels 10.

Note that, the second read period in the first-time image data generation period serves as a first read period in a second-time image data generation period. A second read period in the second-time image data generation period serves as a first read period in a third-time image data generation period.

<Image Acquisition Processing by Radiological-Image Acquisition Device>

Figure 8:
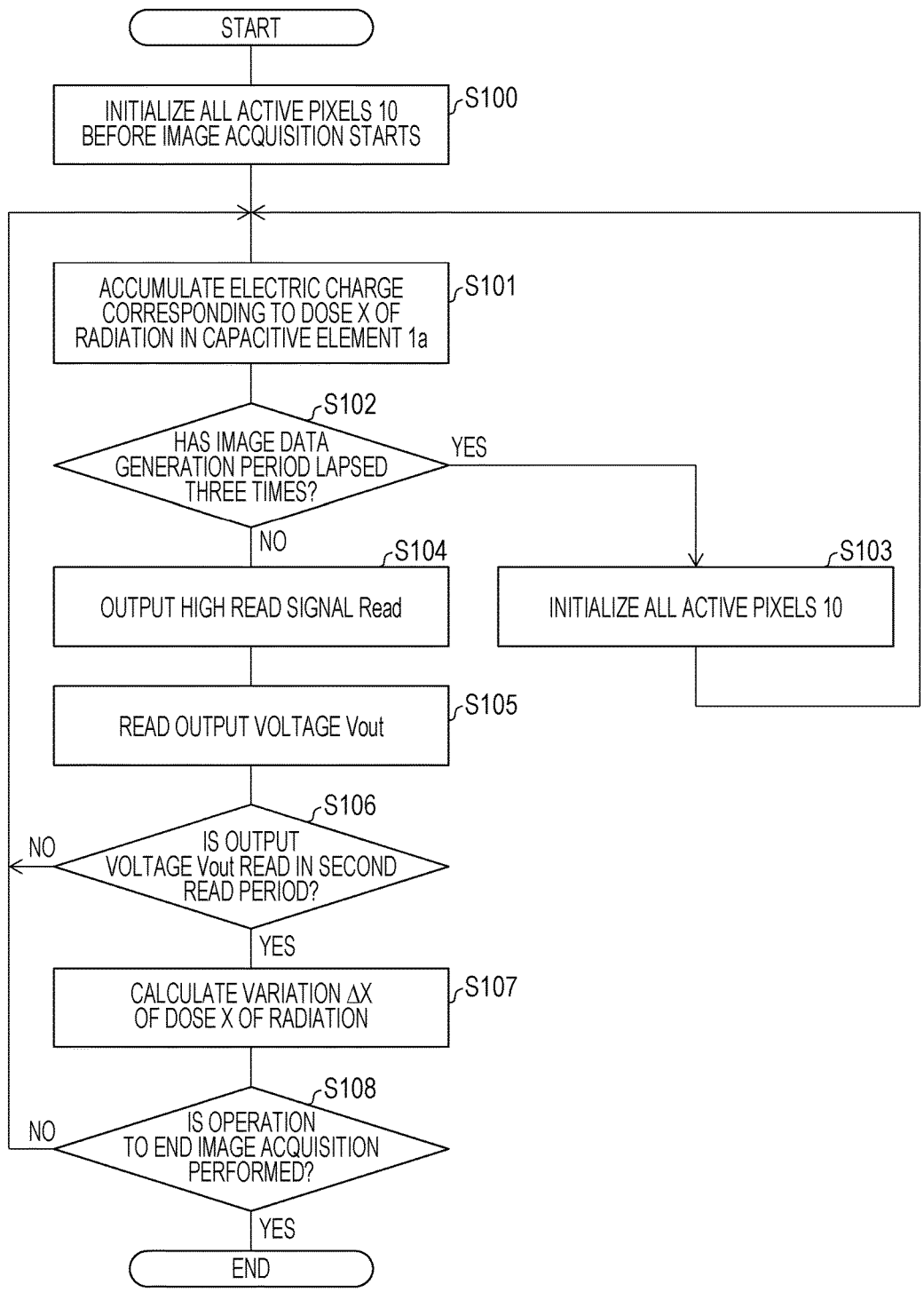
FIG. 8 is a flowchart illustrating image acquisition processing by the radiological-image acquisition device according to Embodiment 1 of the invention.

Next, image acquisition processing by the radiological-image acquisition device 100 will be described with reference to FIG. 8. FIG. 8 is a flowchart illustrating the processing. Note that, a certain active pixel 10 is taken as an example in the following description. Needless to say, similar description is applied to the other active pixels 10.

As illustrated in FIG. 8, first, the reset element control unit 23 outputs a High reset signal Reset_all before image acquisition starts and initializes the active pixel 10 (the other active pixels 10 are also all initialized) (step 100; image acquisition preparation step, hereinafter also abbreviated as S100).

After the image acquisition starts, when radiation that has been radiated to a subject is incident on the active pixel 10, the sensor element 1 accumulates the electric charge corresponding to the dose X of the incident radiation in the capacitive element 1a (S101; electric charge accumulation step).

Next, the reset element control unit 23 determines whether or not an image data generation period has lapsed three times (S102; initialization execution determining step). When determined YES (hereinafter, abbreviated as Y) at S102, the reset element control unit 23 initializes the active pixel 10 (the other active pixels 10 are also all initialized), and the process proceeds to the processing of S101 again (S103 initialization execution step).

On the other hand, when determined NO (hereinafter, abbreviated as N) at S102, the reset element control unit 23 transmits, to the read element control unit 22, a determination result indicating the determination of N. The read element control unit 22 having received the determination result outputs a High read signal Read (S104; read signal output step).

Then, the amplification element 2 and the read element 3 in the active pixel 10 to which the High read signal Read is input are brought into an on state. An output voltage Vout corresponding to the electric charge accumulated in the capacitive element 1a is read from the active pixel 10 via the IV amplifier 24 (S105; output read step). The output voltage Vout that is read is output to the image data generation unit 25.

Next, the image data generation unit 25 determines whether or not the output voltage Vout that is input is read in the second read period (S106; calculation execution determining step). When determined Y at S106, the image data generation unit 25 calculates the variation ΔX of the dose X of the radiation incident on the active pixel 10 on the basis of a difference between the output voltage Vout that is input in the second read period and the output voltage Vout that is input in the first read period and stored in a memory (S107; calculation execution step). Note that, the memory may be incorporated in the image data generation unit 25 or may be externally provided.

On the other hand, when determined N at S106, the image data generation unit 25 causes data of the output voltage Vout that is input to be stored in the memory without executing the calculation of the variation ΔX. Then, the process proceeds to the processing of S101 again.

After the variation ΔX is calculated, the radiological-image acquisition device 100 determines whether or not an operation to end image acquisition is performed by a user (S108; image acquisition end determining step). The determination may be performed by, for example, an image acquisition end determining unit (not illustrated) provided in the radiological-image acquisition device 100. The determination may be performed by, for example, an operation input unit or a power supply switch unit (both of which are not illustrated) also provided in the radiological-image acquisition device 100.

When determined Y at S108, the radiological-image acquisition device 100 ends the image acquisition processing. On the other hand, when determined N at S108, the process proceeds to the processing of S101 again.

In this manner, without initializing all the active pixels 10 altogether in each of the first read period and the second read period, that is, in each of the first frame and the second frame that are sequential frames, the radiological-image acquisition device 100 reads the output voltage Vout corresponding to the first frame and the output voltage Vout corresponding to the second frame from all the active pixels 10. Further, the read operation of the output voltages Vout in the two sequential frames is repeated in the initialization period formed by a plurality of frames. Thus, compared to a case where all the active pixels 10 are initialized for each frame, a frame rate is able to be improved and power consumption is able to be suppressed.

[Embodiment 2]

Another embodiment of the invention will be described below with reference to FIGS. 9 and 10. Note that, for convenience of description, members having the same functions as the members described in the aforementioned embodiment will be given the same reference signs and the description thereof will be omitted.

Figure 9:
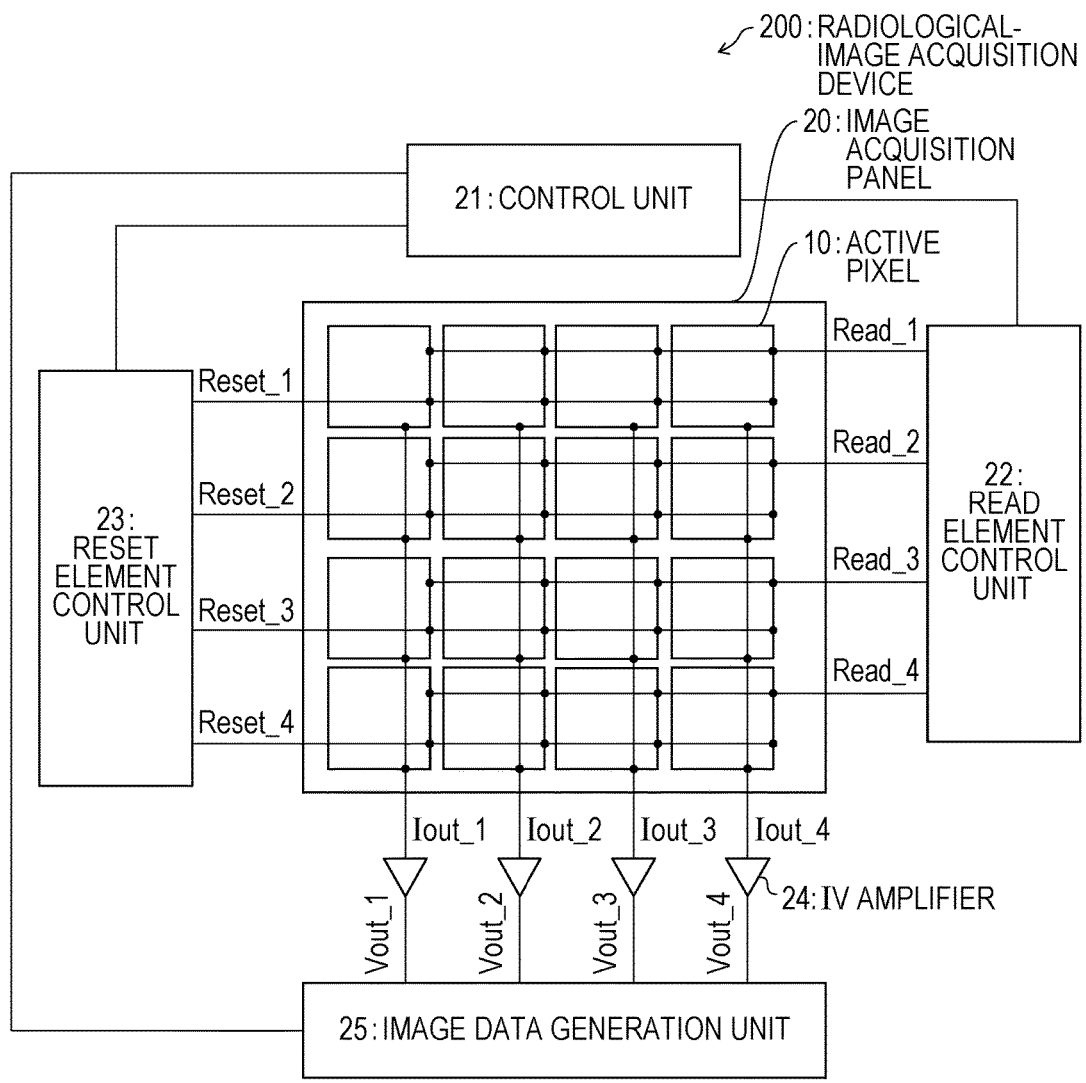
FIG. 9 is a circuit diagram illustrating a main part of a radiological-image acquisition device according to Embodiment 2 of the invention.

As illustrated in FIG. 9, a radiological-image acquisition device 200 according to the present embodiment is different from the radiological-image acquisition device 100 according to Embodiment 1 in that the output terminals of the reset element control unit 23 are connected to the gate electrodes of the read elements 3 of each row of the active pixels 10 and output reset signals Reset_1 to Reset_4. The radiological-image acquisition device 200 is different from the radiological-image acquisition device 100 also in that only four active pixels 10 that form a row are initialized during one frame.

<Image Acquisition Operation by Radiological-Image Acquisition Device>

An image acquisition operation by the radiological-image acquisition device 200 will be described below with reference to FIG. 10. FIG. 10 illustrates a timing chart of the image acquisition operation by the radiological-image acquisition device 200.

Figure 10:
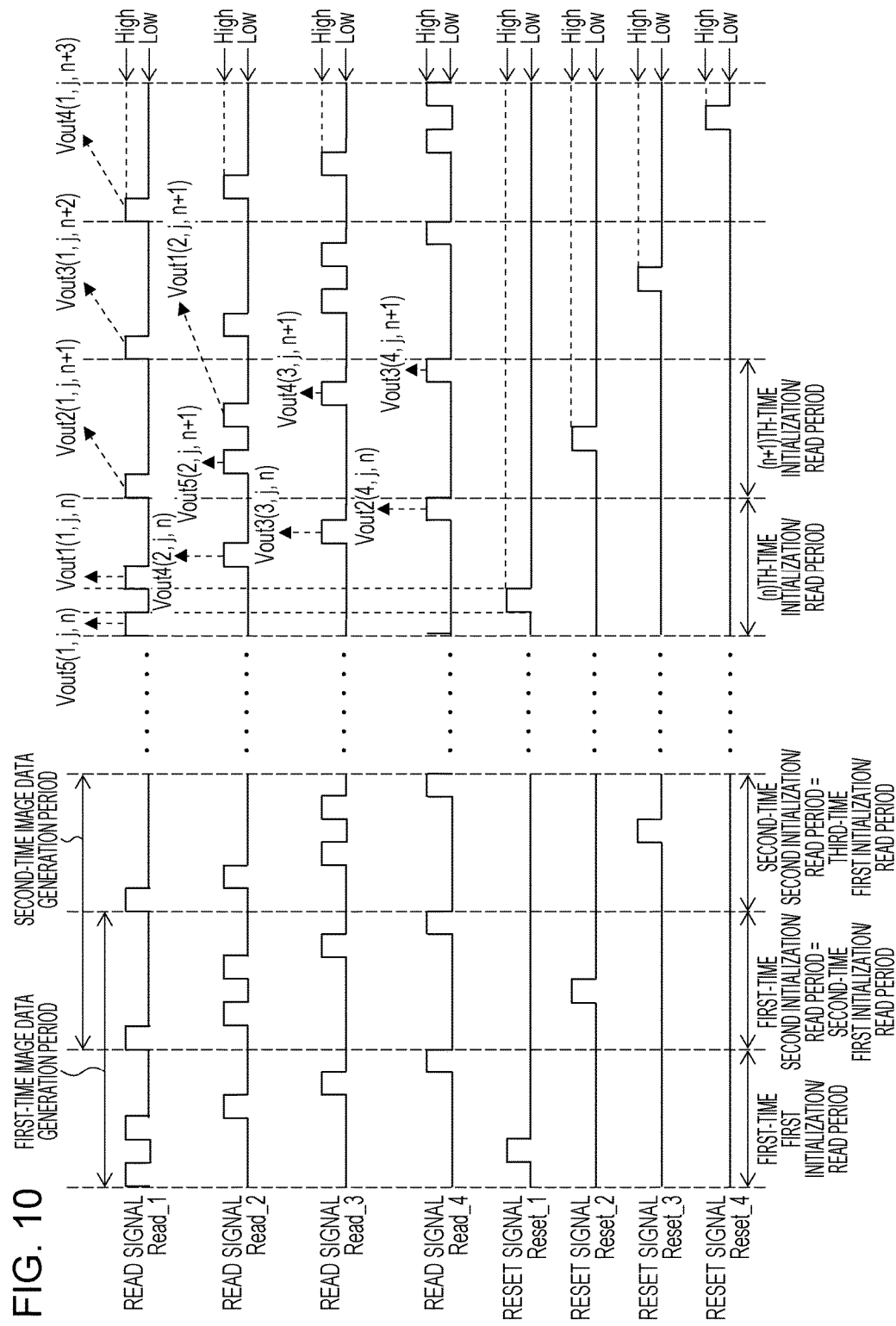
FIG. 10 illustrates a timing chart of an image acquisition operation by the radiological-image acquisition device according to Embodiment 2 of the invention.

The image acquisition operation by the radiological-image acquisition device 200 is constituted by a phase of an image data generation period as illustrated in FIG. 10. The image data generation period is constituted by two phases of a first initialization/read period and a second initialization/read period and both the periods have a time length of one frame. Further, the first initialization/read period serves as a first frame and the second initialization/read period serves as a second frame. Note that, though an additional period for signal accumulation is not set between respective frames in the present embodiment, it is needless to say that the additional period may be set.

First, the read element control unit 22 sequentially outputs first-time High read signals Read_1, Read_2, Read_3, and Read_4 from the respective output terminals. At this time, the read element control unit 22 controls the output of the signals so that only the read signal Read_1 has a High period temporarily suspended.

Next, the reset element control unit 23 outputs a first-time High reset signal Reset_1 so that initialization of the respective active pixels 10 of a first row starts at a time when a first-half High period of the first-time read signal Read_1 is suspended. That is, fall of the first-half High period of the first-time read signal Read_1 is synchronized with rise of the first-time High reset signal Reset_1.

Then, the read element control unit 22 controls the output of the signals so that a second-half High period of the first-time read signal Read_1 restarts at a time when the High period of the first-time reset signal Reset_1 ends. That is, fall of the first-time High reset signal Reset_1 is synchronized with rise of the second-half High period of the first-time read signal Read_1.

Note that, the active pixels 10 are initialized during a period when the read of the output voltage Vout is suspended in the present embodiment. However, there is no limitation to such a method of read and initialization, and the initialization of the active pixels 10 may be performed at the same time during a period when the High period of the first-time reset signal Reset_1 is not suspended but continued, for example.

Here, in each of the active pixels 10 to be initialized in the first row, an output voltage read immediately before the initialization is set as Vout5(1, j, 1) and an output voltage read immediately after the initialization is set as Vout1(1, j, 1). In addition, in each of the active pixels 10 of the other rows, output voltages that are read are set as Vout4(2, j, 1), Vout3(3, j, 1), and Vout2(4, j, 1).

The respective output voltages Vout that are read are output to the image data generation unit 25. When all the output voltages Vout are input to the image data generation unit 25, a first-time first initialization/read period ends.

After the first-time first initialization/read period ends, a first-time second initialization/read period starts. Specifically, the read element control unit 22 outputs second-time read signals Read so that only the read signal Read_2 has the High period temporarily suspended.

The reset element control unit 23 outputs the second-time High reset signal Reset 2 so that initialization of the respective active pixels 10 of a second row is performed after the High period of the second-time read signal Read_2 is suspended.

Here, in each of the active pixels 10 of the second row, an output voltage read immediately before the initialization is set as Vout5(2, j, 2) and an output voltage read immediately after the initialization is set as Vout1(2, j, 2). In addition, in each of the active pixels 10 of the other rows, output voltages that are read are set as Vout2 (1, j, 2), Vout4(3, j, 2), and Vout3(4, j, 2). The respective output voltages Vout that are read are output to the image data generation unit 25.

Next, the image data generation unit 25 generates data for one two-dimensional image on the basis of the output voltages Vout that are read in the first-time first initialization/read period and the output voltages Vout that are read in the first-time second initialization/read period.

That is, in each of the active pixels 10 of the first row, when an output voltage of the active pixel 10 of the first row and the (j)th column read in a first-time second-half High period of the read signal Read_1 is set as Vout1(1, j, 1) and an output voltage read in a second-time High period of the read signal Read_1 is set as Vout2(1, j, 2), a relation of Vout2(1, j, 2)−Vout1(1, j, 1)=α{X(1, j, 2)−X(1, j, 1)} is satisfied. Thus, in each of the active pixels 10 of the first row, by performing calculation of Vout2(1, j, 2)−Vout1(1, j, 1), the image data generation unit 25 calculates the variation ΔX of the dose X of the radiation incident on the active pixel 10 from the first initialization/read period to the second initialization/read period.

As described above, when the image data generation unit 25 acquires data for one two-dimensional image having the resolution of 4×4, the first-time second initialization/read period ends and the first-time image data generation period ends.

Also in second-time and subsequent image data generation periods, the image data generation unit 25 acquires data for two-dimensional images having the resolution of 4×4 one by one in a similar manner to the aforementioned manner.

That is, in a case where the active pixels 10 of the (i)th row are initialized during an (n)th-time initialization/read period, when an output voltage of the active pixel 10 of the (i)th row and the (j)th column read in an (n)th-time second-half High period of the read signal Read_i is set as Vout1(i, j, n) and an output voltage read in an (n+1)th-time High period of the read signal Read_i is set as Vout2(i, j, n+1), a relation of Vout2(i, j, n+1)−Vout1(i, j, n)=α{X(i, j, n+1)−X(i, j, n)} is satisfied. Thus, by performing calculation of Vout2(i, j, n+1)−Vout1(i, j, n), the variation ΔX in the active pixels 10 of the (i)th row is calculated.

Note that, a second initialization/read period in an (n)th-time image data generation period serves as a first initialization/read period in an (n+1)th-time image data generation period.

In this manner, the reset element control unit 23 of the radiological-image acquisition device 200 initializes the active pixels 10 of different rows for each frame. Since at least any of the active pixels 10 is initialized for each frame, a period during which generation of the two-dimensional image data is stopped in order to initialize all the active pixels 10 altogether does not need to be provided. This makes it possible to continuously generate data for a plurality of two-dimensional images without interruption and ensure constancy of a frame cycle without providing an additional period for signal accumulation, that is, a redundant period as in Embodiment 1.

Note that, since the actual number (i×j) of the active pixels 10 included in the radiological-image acquisition device according to the invention is significantly greater than 4×4, the active pixels 10 of a plurality of rows (for example, several tens of rows) are actually initialized in one frame among a plurality of frames that constitute an initialization cycle.

[Embodiment 3]

Another embodiment of the invention will be described below with reference to FIGS. 11 and 12. Note that, for convenience of description, members having the same functions as the members described in the aforementioned embodiment will be given the same reference signs and the description thereof will be omitted.

A radiological-image acquisition device 300 according to the present embodiment is different from the radiological-image acquisition device 100 or 200 according to Embodiment 1 or 2 in that the image data generation unit 25 uses an approximation function by which a relation between the dose X of radiation incident on the active pixel 10 and the output voltage Vout read from the active pixel 10 is indicated and calculates the variation ΔX of the dose X of the radiation.

Note that, a configuration of a main part of the radiological-image acquisition device 300 is the same as a configuration of a main part of the radiological-image acquisition device 100 according to Embodiment 1. Control of signal output by the read element control unit 22 and the reset element control unit 23 that are included in the radiological-image acquisition device 300 is also the same as that of the radiological-image acquisition device 100 (refer to FIG. 5). However, the configuration or the like of the main part of the radiological-image acquisition device 300 may be the same as, for example, that of the radiological-image acquisition device 200 according to Embodiment 2.

<Calculation of Variation of Radiation Dose by Image Data Generation Unit>

Figure 11:
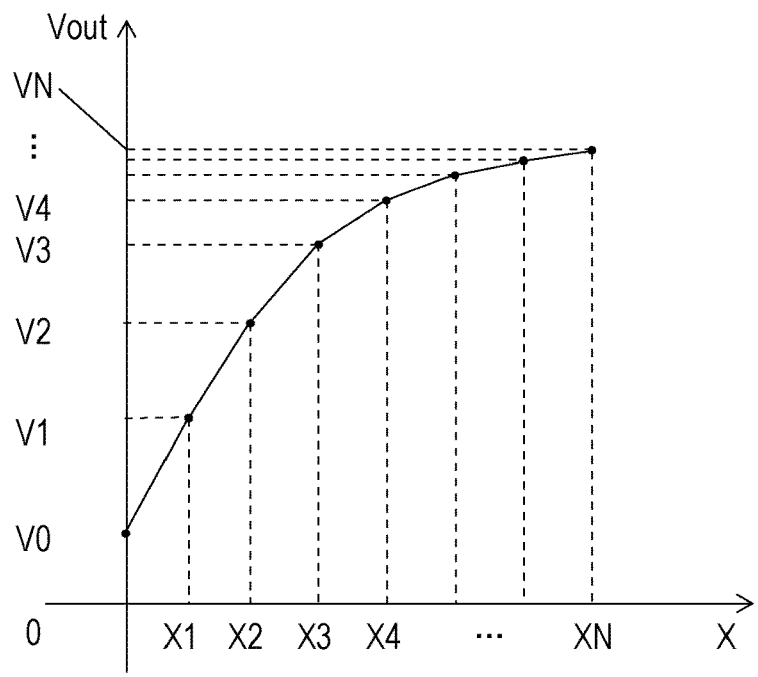
FIG. 11 is a graph indicating a relation between a dose of radiation incident on an active pixel included in a radiological-image acquisition device according to Embodiment 3 of the invention and an output voltage read from the active pixel.
Figure 12:
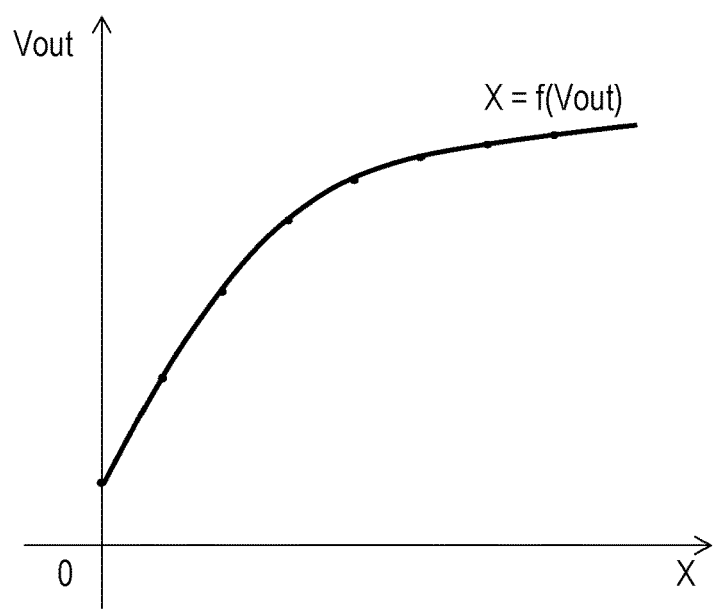
FIG. 12 is a graph indicating a relation between the dose of radiation and the output voltage by an approximation function.

With reference to FIGS. 11 and 12, calculation of the variation ΔX of the dose X of the radiation by the image data generation unit 25 will be described below. FIG. 11 is a graph indicating a relation between the dose X of the radiation incident on the active pixel 10 included in the radiological-image acquisition device 300 and the output voltage Vout read from the active pixel 10. FIG. 12 is a graph indicating a relation between the dose X of the radiation and the output voltage Vout by an approximation function.

When the dose X of the radiation incident on the active pixel 10 and the output voltage Vout which is read from the active pixel 10 and corresponds to the dose X are actually measured, nonlinearity appears as illustrated in FIG. 11. Such a phenomenon is caused because a relation between a gate voltage and a drain current of the amplification element 2 is not linear and characteristic of the sensor element 1 depends on a voltage between terminals.

Further, when the image acquisition operation is repeated without initializing the active pixel 10, a quantity of the electric charge accumulated in the capacitive element 1a increases, so that a variation width of the gate voltage of the amplification element 2 also increases accordingly, resulting that nonlinearity appears more markedly.

Thus, in order to calculate the variation ΔX of the dose X of the incident radiation more accurately from the output voltage Vout, it is necessary to derive an approximation function by which a relation between the output voltage Vout and the dose X of the radiation is corrected to nonlinearity that is close to the actual measurement and calculate the variation ΔX by using the approximation function. A method for deriving the approximation function will be described below.

(Method for Deriving Approximation Function)

First, a surface of the image acquisition panel 20, on which the active pixels 10 are arranged, is continuously irradiated with a certain dose of radiation uniformly. For a certain active pixel 10, the output voltages Vout are read for each certain frame (which may be for each frame or for each several frames) in such a manner that the output voltages are V0 immediately after initialization, and then V1, V2, V3, V4, . . . , and VN. On the basis of data of the output voltages Vout that are read, a relation between the dose X of the radiation and each of the output voltages Vout corresponding to the dose X is made into a graph as illustrated in FIG. 11.

In the graph, X1, X2, X3, X4, . . . , and XN each represents the dose X of the radiation incident on the certain active pixel 10. In this case, the output voltages Vout are read for each certain frame by radiation with the certain dose, and thus do not need to be represented by absolute values thereof and may be represented by any method so as to satisfy X1=X2−X1=X3−X2=X4−X3= . . . =XN−XN−1.

Next, in the relation between the dose X of the radiation and the output voltage Vout corresponding to the dose X illustrated in FIG. 11, X is considered as a function of Vout, so that the approximation function X=f(Vout) as indicated with a graph of FIG. 12 is derived. The approximation function X=f(Vout) is able to be derived, for example, as a polygonal line approximation obtained by connecting points (0, V0), (X1, V1), . . . , (XV, VN) by straight line in the graph of FIG. 11. The approximation function X=f(Vout) may be derived by using, for example, a polynomial approximation, a least square method, or the like.

The derived approximation function X=f(Vout) is associated as an expression for calculating the variation ΔX of the dose X of the incident radiation in all the active pixels 10 and stored in the memory (not illustrated) incorporated in the image data generation unit 25. The memory may be provided outside the image data generation unit 25.

Note that, approximation functions X=f(Vout) may be derived individually for the respective active pixels 10. In other words, the image data generation unit 25 may use the approximation functions X=f(Vout) corresponding to all the respective active pixels 10. Use of the approximation functions X=f(Vout) for the respective active pixels 10 makes it possible to calculate the variation ΔX of the dose X of the radiation more accurately. In this case, all expressions of the approximation functions X=f(Vout) for the respective active pixels 10 are stored in the memory of the image data generation unit 25.

A graph may be created by averaging the relations between the dose X of the radiation for each of the active pixels 10 and the output voltage Vout corresponding to the dose X and the approximation function X=f(Vout) derived on the basis of the graph may be associated with all the active pixels 10.

Further, the approximation function X=f(Vout) may be derived through an experiment or the like by a user. Alternatively, an approximation function deriving unit (not illustrated) may be provided inside or outside the image data generation unit 25 so that the approximation function X=f(Vout) is automatically derived by the radiation being incident on the active pixel 10.

(Calculation of Variation of Radiation Dose with Use of Approximation Function)

The image data generation unit 25 calculates the variation ΔX of the dose X of the radiation incident on the active pixel 10 by using the approximation function X=f(Vout) derived by the method described above.

That is, when an output voltage of the active pixel 10 of the (i)th row and the (j)th column read in the (n)th-time High period of the read signal Read_i is set as Vout(i, j, n) and an output voltage read in the (n+1)th-time High period of the read signal Read_i is set as Vout(i, j, n+1), a relation of f(Vout(i, j, n+1))−f(Vout(i, j, n))=X(i, j, n+1)−X(i, j, n) is satisfied. Thus, by performing calculation of f(Vout(i, j, n+1))−f(Vout(i, j, n)), the variation ΔX is calculated.

In this manner, since the image data generation unit 25 calculates the variation ΔX of the dose X of the radiation incident on the active pixel 10 by using the approximation function X=f(Vout), the calculated variation ΔX has a value close to an actual measurement value. Accordingly, the radiological-image acquisition device 300 is able to acquire two-dimensional image data with higher accuracy.

[Implementation Example by Software]

A control block (particularly, the read element control unit 22 and the reset element control unit 23) of the radiological-image acquisition device 100 may be realized by a logic circuit (hardware) formed in an integrated circuit (IC chip) or the like, or may be realized with software by using a CPU (Central Processing Unit).

In the case of realizing with software, the radiological-image acquisition device 100 includes the CPU which executes a command of a program which is software for realizing each function, a ROM (Read Only Memory) or a storage device (each of which is referred to as a "recording medium") in which the program and various data are recorded so as to be readable by a computer (or the CPU), a RAM (Random Access Memory) which develops the program, and the like. When the computer (or the CPU) reads the program from the recording medium for execution, an object of the invention is achieved. As the recording medium, it is possible to use a "non-transitory tangible medium" such as, for example, a tape, a disk, a card, a semiconductor memory, or a programmable logic circuit. Moreover, the program may be supplied to the computer via any transmission medium (a communication network, a broadcast wave, or the like) by which the program is able to be transmitted. Note that, the invention may be realized also in a form of a data signal in which the program is embodied by electronic transmission and which is embedded in a carrier wave.

[Conclusion]

A radiological-image acquisition device (100, 200, 300) according to an aspect 1 of the invention is a radiological-image acquisition device that acquires a two-dimensional image according to a dose (X) of radiation that has been radiated to a subject, and includes: a plurality of pixels (active pixels 10) disposed two-dimensionally; a capacitive element (1a) in each of the plurality of pixels, and, when the radiation is incident on the plurality of pixels, accumulates electric charge corresponding to the dose for the pixel in at least two sequential frames; and a read control unit (read element control unit 22, reset element control unit 23) that, with respect to at least one pixel of the plurality of pixels, does not perform initialization of the at least one pixel but reads, from the pixel, a first output (output voltage Vout) and a second output (output voltage Vout) which correspond to the accumulated electric charge in each of a first frame and a second frame that constitute the two frames.

According to the aforementioned configuration, the read control unit does not perform the initialization of at least one pixel of the plurality of pixels disposed two-dimensionally but reads, from the pixel, the first output and the second output which correspond to the electric charge accumulated in the capacitive element in each of the first frame and the second frame that constitute the two frames. Here, "one frame" refers to a time required to read data for one two-dimensional image from the plurality of pixels that are disposed two-dimensionally.

Thus, it is not necessary for at least one pixel that is not subjected to the initialization to consider a time required to perform the initialization. Therefore, compared to a case where a plurality of pixels are all initialized for each frame, a total time for acquiring two-dimensional image data is able to be reduced and power consumption required for the initialization of the at least one pixel is able to be reduced.

Accordingly, it is possible to provide the radiological-image acquisition device that realizes improvement of a frame rate and suppression of power consumption.

In the radiological-image acquisition device (100, 200, 300) according to an aspect 2 of the invention, in the aspect 1, an initialization cycle in which each of the plurality of pixels (active pixels 10) is subjected to the initialization may be defined as a time length of a plurality of frames, and the read control unit (reset element control unit 23) may perform the initialization of each of the plurality of pixels within the initialization cycle so that all the plurality of pixels are subjected to the initialization before the initialization cycle ends.

A quantity of the electric charge, to be accumulated in the capacitive element, of the pixel that is not subjected to the initialization but is subjected to the read of the first output and the second output among the plurality of pixels increases in accordance with the number of repetition times of the read. When the quantity of the accumulated electric charge reaches a predetermined quantity through a plurality of frames, the capacitive element is brought into a saturated state in which no more electric charges are able to be accumulated, so that the first output and the second output that are read after reaching the predetermined quantity are saturated. Thus, after the predetermined quantity is reached, the first output and the second output that are read do not correspond to the dose of the radiation that has been radiated to the subject.

On the other hand, when each of the plurality of pixels is initialized in a cycle of one frame and all the plurality of pixels are initialized in one frame, a time of one frame becomes long.

Meanwhile, according to the aforementioned configuration, all the plurality of pixels are initialized over a time of a plurality of frames, it is possible to reduce the time of one frame compared to the case where all the plurality of pixels are initialized in one frame. As a result, the radiological-image acquisition device is able to read the first output and the second output which correspond to the dose of the radiation while reducing the time of one frame.

In the radiological-image acquisition device (100, 200) according to an aspect 3 of the invention, in the aspect 1 or 2, each of the plurality of pixels (active pixels 10) may further include an amplification element (2) that amplifies the first output or the second output, the read control unit (read element control unit 22) may read, from each of the plurality of pixels, a second amplification output (output voltage Vout) obtained by amplifying the second output and a first amplification output (output voltage Vout) obtained by amplifying the first output, and an output generation unit (image data generation unit 25) that generates a read output (variation ΔX) corresponding to the dose (X) of the radiation by obtaining a difference between the second amplification output and the first amplification output that are read by the read control unit may be further included.

According to the aforementioned configuration, each of the plurality of pixels further includes the amplification element that amplifies the first output or the second output, and the read control unit reads, from each of the plurality of pixels, the second amplification output obtained by amplifying the second output and the first amplification output obtained by amplifying the first output. Therefore, even when noise or the like is generated in the read control unit, the radiological-image acquisition device is able to more reliably read the outputs from each of the plurality of pixels as the first amplification output and the second amplification output.

Moreover, according to the aforementioned configuration, the radiological-image acquisition device further includes the output generation unit that generates the read output corresponding to the dose of the radiation that has been radiated to the subject by obtaining the difference between the second amplification output and the first amplification output. Therefore, even when, in two frames corresponding to read of the first amplification output and the second amplification output, a pixel to be subjected to the read is not initialized, by using the read output, the radiological-image acquisition device is able to obtain, as a value close to an actual measurement value, the dose of the radiation incident on the pixel from the read of the first amplification output to the read of the second amplification output.

Further, according to the aforementioned configuration, image data of each frame is able to be obtained by subtracting an output read immediately after the initialization from an output read after an accumulation period of the electric charge. Since noise accumulated in a pixel during the initialization is removed by such a read operation using double sampling, the radiological-image acquisition device is able to acquire the image data having less noise.

In the radiological-image acquisition device (300) according to an aspect 3 of the invention, in any of the aspects 1 to 3, the output generation unit (image data generation unit 25) may use an approximation function (X=f(Vout)) that indicates a relation between a dose (X) of radiation continuously radiated to a certain pixel (active pixel 10) subjected to the initialization and an output (output voltage Vout) corresponding to electric charge accumulated in the capacitive element (1a) corresponding to the dose, may obtain a difference between a second correction output (f(Vout)) obtained by substituting the second amplification output (output voltage Vout) to the approximation function and a first correction output (f(Vout)) obtained by substituting the first amplification output (output voltage Vout) to the approximation function, and may generate the read output (variation $\Delta X$).

According to the aforementioned configuration, the output generation unit uses the approximation function that indicates the relation between the dose of the radiation continuously radiated to the certain pixel subjected to the initialization and the output corresponding to the electric charge accumulated in the capacitive element corresponding to the dose, obtains the difference between the second correction output obtained by substituting the second amplification output to the approximation function and the first correction output obtained by substituting the first amplification output to the approximation function, and thereby generates the read output.

As the approximation function represents the relation between the dose of the radiation incident on the pixel and the output from the pixel corresponding to the dose in a form close to actual measurement, the first correction output and the second correction output have values closer to an actual measurement value of the dose of the radiation that has been radiated to the subject. Thus, compared to a case of obtaining a difference between the second amplification output and the first amplification output, the output generation unit is able to generate the read output with a value closer to an actual measurement value.

In the radiological-image acquisition device (300) according to an aspect 5 of the invention, in the aspect 4, the output generation unit (image data generation unit 25) may use the approximation function (X=f(Vout)) corresponding to each of the plurality of pixels (active pixels 10).

The relation between the dose of the radiation incident on the pixel and the output from the pixel corresponding to the dose varies between the plurality of pixels because of a difference of characteristics of elements provided in the pixels, a difference of locations where the pixels are disposed on an image acquisition panel, or the like.

Meanwhile, according to the aforementioned configuration, the output generation unit generates read outputs for the plurality of pixels by using the approximation function corresponding to each of the plurality of pixels. Therefore, for example, compared to a case where the approximation function corresponding to a certain pixel is applied as approximation functions of the other pixels, the output generation unit is able to generate each of the read outputs with a value closer to an actual measurement value of each of the pixels.

A radiological-image acquisition method according to an aspect 6 of the invention is a radiological-image acquisition method for acquiring a two-dimensional image according to a dose (X) of radiation that has been radiated to a subject, and includes: an electric charge accumulation step (S101) of, when the radiation is incident on a plurality of pixels (active pixels 10) that are disposed two-dimensionally, accumulating electric charge corresponding to the dose for each of the pixels in at least two sequential frames; and an output read step (S105) of, with respect to at least one pixel of the plurality of pixels, not performing initialization of the at least one pixel but reading, from the pixel, a first output (output voltage Vout) and a second output (output voltage Vout) which correspond to the accumulated electric charge in each of a first frame and a second frame that constitute the two frames.

According to the aforementioned configuration, it is possible to provide the radiological-image acquisition method that realizes improvement of a frame rate and suppression of power consumption.

The radiological-image acquisition device (100, 200, 300) according to each of the aspects of the invention may be realized by a computer, and, in this case, a program which causes the computer to operate as the respective units (limited to software elements) provided in the radiological-image acquisition device to thereby realize the radiological-image acquisition device in the computer, and a computer readable recording medium which stores the program therein are also included in the scope of the invention.

According to the aforementioned configuration, it is possible to provide a program and a recording medium that enable radiological-image acquisition in which a frame rate is improved and power consumption is suppressed.

The invention is not limited to each of the embodiments described above, and may be modified in various manners within the scope of the claims and an embodiment achieved by appropriately combining technical means disclosed in each of different embodiments is also encompassed in the technical scope of the invention. Further, by combining the technical means disclosed in each of the embodiments, a new technical feature may be formed.

REFERENCE SIGNS LIST 1a capacitive element
2 amplification element
10 active pixel (pixel)
22 read element control unit (read control unit)
23 reset element control unit (read control unit)
25 image data generation unit (output generation unit)
100, 200, 300 radiological-image acquisition device

The invention claimed is:
1. A radiological-image acquisition device that acquires a two-dimensional image according to a dose of radiation that has been radiated to a subject, the radiological-image acquisition device comprising:
 a plurality of pixels disposed two-dimensionally;
 a capacitive element in each of the plurality of pixels, the capacitive element, when the radiation is incident on each of the plurality of pixels, accumulating electric charge corresponding to the dose for each of the pixels in at least two sequential frames; and
 a read control unit that, with respect to at least one of the plurality of pixels, does not perform initialization of the at least one pixel but reads, from the pixel, a first output and a second output which correspond to the accumulated electric charge in each of a first frame and a second frame that constitute the at least two sequential frames, wherein an initialization cycle in which each of the plurality of pixels is subjected to the initialization is defined as a time length of a plurality of frames, and the read control unit performs the initialization of each of the plurality of pixels within the initialization cycle so that all the plurality of pixels are subjected to the initialization before the initialization cycle ends, the initialization of the each of the plurality of pixels being performed such that a pixel(s) of the plurality of pixels, which is/are subjected to the initialization, is/are different from frame to frame in the plurality of frames.

2. The radiological-image acquisition device according to claim 1, wherein each of the plurality of pixels further includes an amplification element that amplifies the first output or the second output, the read control unit reads, from each of the plurality of pixels, a second amplification output obtained by amplifying the second output and a first amplification output obtained by amplifying the first output, and an output generation unit that generates a read output corresponding to the dose of the radiation by obtaining a difference between the second amplification output and the first amplification output that are read by the read control unit is further included.

3. The radiological-image acquisition device according to claim 2, wherein the output generation unit uses an approximation function that indicates a relation between a dose of radiation continuously radiated to a certain pixel subjected to the initialization and an output corresponding to electric charge accumulated in the capacitive element corresponding to the dose, obtains a difference between a second correction output obtained by substituting the second amplification output to the approximation function and a first correction output obtained by substituting the first amplification output to the approximation function, and generates the read output.

4. The radiological-image acquisition device according to claim 3, wherein the output generation unit uses the approximation function corresponding to each of the plurality of pixels.

* * * * *